United States Patent [19]

Tomoff

[11] 4,294,127
[45] Oct. 13, 1981

[54] AUTOMATIC SAMPLE FEEDER FOR FLAMELESS ATOMIC ABSORPTION SPECTROMETER

[75] Inventor: Toma Tomoff, Überlingen, Fed. Rep. of Germany

[73] Assignee: Bodenseewerk Perkin-Elmer & Co., GmbH, Fed. Rep. of Germany

[21] Appl. No.: 154,208

[22] Filed: May 29, 1980

[30] Foreign Application Priority Data

Jun. 15, 1979 [DE] Fed. Rep. of Germany ....... 2924124

[51] Int. Cl.³ ............................................. G01N 35/06
[52] U.S. Cl. ............................... 73/864.21; 73/864.25; 422/64; 422/100
[58] Field of Search .................. 73/423 A; 422/62, 63, 422/64, 65, 81, 82, 99, 100, 102

[56] References Cited

U.S. PATENT DOCUMENTS

| | | | |
|---|---|---|---|
| 3,134,263 | 5/1964 | DeJong | 73/423 A |
| 3,192,968 | 7/1965 | Baruch et al. | 422/64 |
| 3,348,691 | 10/1967 | Travaglio | 73/423 A |
| 4,102,368 | 7/1978 | Marfurt | 422/64 |

*Primary Examiner*—S. Clement Swisher
*Attorney, Agent, or Firm*—S. A. Giarratana; F. L. Masselle; R. A. Hays

[57] ABSTRACT

Apparatus for injecting a selected one of a plurality of samples into a graphite tube atomizer of a flameless atomic absorption spectrometer. A sample dilutant or blank solution, a standard solution for calibrating the spectrometer, and each of a plurality of unknown sample solutions are continuously fed into separate overflow vessels mounted in a turntable driven by a servomotor and monitored by a suitable analog-to-digital encoder. Each of the vessels overflow into a common drain channel and the vessels are positioned by a control system so that a small sample from selected vessels that may contain an unknown sample, dilutant, or calibrating standard, is drawn by a pump into an intake tube. A servomechanism then repositions the tube into the graphite tube atomizer and the pump reverses to inject the solution into the atomizer. The control system is programmed to operate in proper sequence: the spectrometer, the intake tube servomotor, and also to position the turntable and operate the intake tube pump as well as a rinse pump that flushes the entire input tube. The dilutant and standard solutions are supplied from large containers positioned on weight monitors that produce alarms when the solutions are nearly exhausted. This alarm system, together with automatic sample feeding and the use of the overflow vessels on the turntable, eliminates the need for continual manual monitoring by a technician.

4 Claims, 3 Drawing Figures

AUTOMATIC SAMPLE FEEDER FOR FLAMELESS ATOMIC ABSORPTION SPECTROMETER

CROSS-REFERENCE TO RELATED APPLICATIONS

The invention described and claimed herein is related to copending patent application Ser. No. 102,704 filed Dec. 12, 1979, and is an automated improvement thereto.

BRIEF SUMMARY OF THE INVENTION

This invention relates to automatic sampling apparatus for analytical equipment and, in particular, to sampling apparatus for flameless atomic absorption spectrometers.

The structure of the sample feeding apparatus described and claimed herein is substantially the same as that described in copending patent application Ser. No. 102,704 filed Dec. 12, 1979. That prior art application describes a turntable containing a plurality of sample vessels that is positioned by a control system and monitored by an optical encoder. A sample pump is coupled to a sample intake tube, the opposite or free end of which is positioned by a servomotor operated lever into the sample vessels in the turntable which are selected by the positioning of the turntable. When a small sample has been drawn into the intake tube, the servomotor operates its lever to extend the end of the tube into the sample input opening of a graphite tube atomizer in an adjacent atomic absorption spectrometer. The entire turntable is then pivoted aside to a second position so that when the intake tube is returned to its intake position, it enters a rinsing vessel located on the movable base plate of the turntable. A rinse solution pump then flushes a rinse solution through the entire intake tube and into the rinsing vessel. The cleaned intake tube is then lifted by the lever, the turntable is pivoted to a third position, and the intake tube is again positioned into a vessel containing a dilutant reagent which is then inserted into the graphite tube atomizer. The atomic absorption spectrometer is then started in the conventional manner. In the meantime, however, the turntable is returned to its second position and is again flushed with the rinsing solution so that it will be ready to transfer the next sample from the turntable vessels. All pumps, servomotors, and the atomic absorption spectrometer are operated in proper sequence by the associated control system.

In the above described prior art sample feeding system, all vessels in the turntable are simple cylindrical vessels which are manually filled with either a standard solution used for calibration of the spectrometer, or the unknown sample mixed with the proper amount of its dilutant solution. It is apparent, therefore, that the system requires an attendant technician who must continually monitor the contents of the vessels and refill them as necessary.

The present invention is a substantial improvement over the above described prior art sample feeding apparatus because all functions are performed automatically and therefore require very little time of an attendant technician.

Briefly described, the apparatus of the present invention includes the position controlled turntable, intake tube, rinse and sample pumps, and the servomotors of the above described prior art. The improvement thereto includes the use, in the turntable, of overflow type of vessels which receive a continuous flow of samples from a corresponding number of input conduits and overflow all excess into a drain channel beneath the turntable. Continuously flowing sample solutions also result in an improvement over the prior art since the continuous sample flow prevents any separation or settling of the fluids in the turntable vessels so that a more accurate analysis may be made therefrom. The standard calibration solutions and the dilutant or blank solution, which also serves as a rinse for flushing the intake tube, are also pumped into separate turntable overflow vessels from large supply vessels mounted on platforms of weight monitors that produce alarm signals, preferably audible, when the quantity of the solutions drops below a predetermined level.

DETAILED DESCRIPTION OF THE DRAWINGS

In the drawings which illustrate the preferred embodiment of the invention:

DETAILED DESCRIPTION

Figure 1:
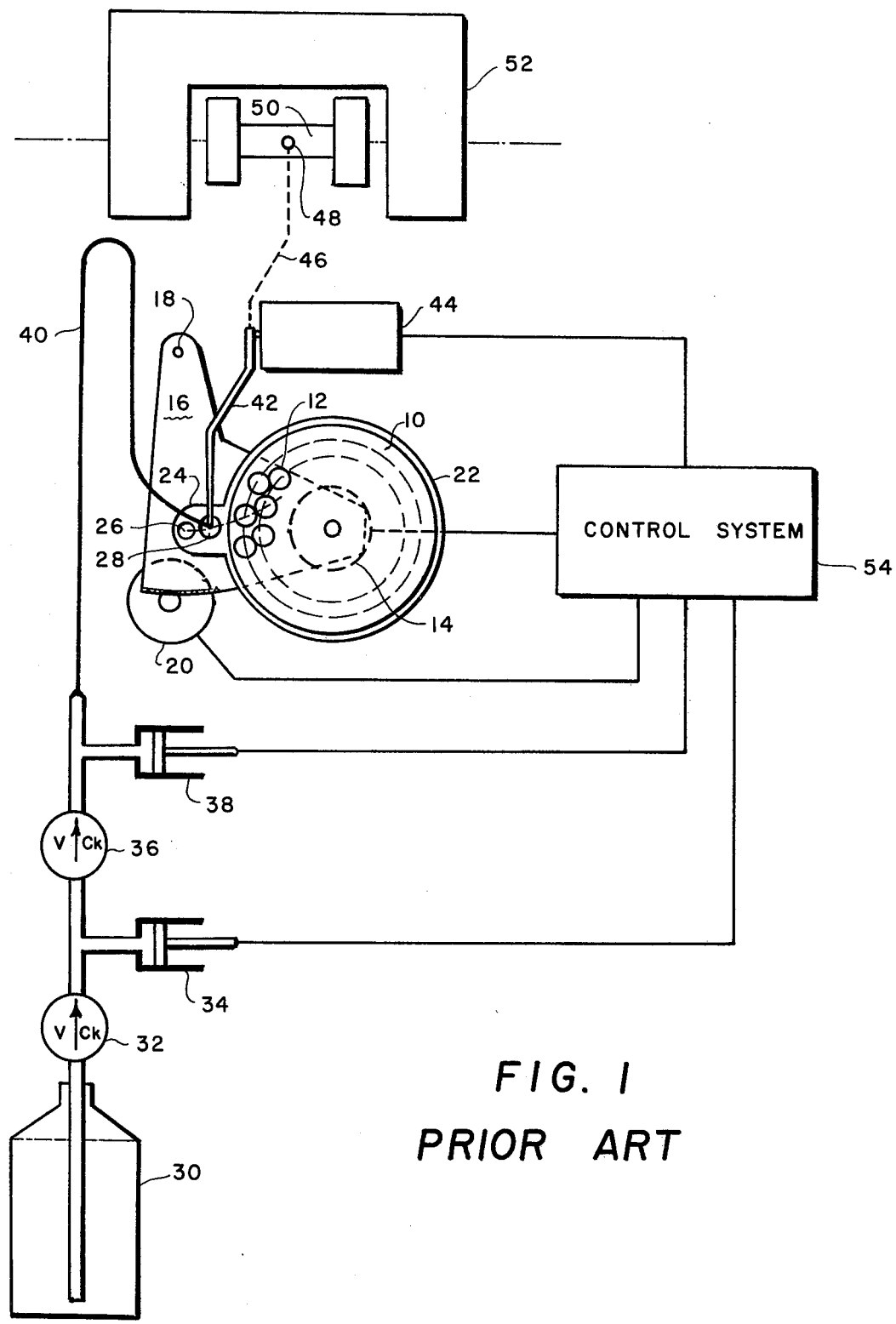
FIG. 1 is a schematic diagram of the prior art sample feeding apparatus.

FIG. 1 is a schematic diagram of the prior art system which, as previously explained, contains structure which is substantially similar to that contained in the present improvement. In FIG. 1, a turntable 10 contains a plurality of small sample vessels 12 arranged in concentric rows of the turntable. Turntable 10 is rotated by a servomotor 14 and the turntable, together with the servomotor 14, is mounted to a turntable carrier plate 16 which is rotatable about a pivot 18 and is gear driven through a short arc by a servomotor 20.

Turntable 10 is contained within a housing 22 which contains, in an area 24 outside of the turntable 10, a reagent vessel 26 and an overflow type of rinsing vessel 28 which is arranged to overflow through a conduit into a drain system (not shown).

A fluid container 30, which contains a supply of rinsing liquid is coupled through a check valve 32 to a rinse pump 34 operated by a stepping motor (not shown). The output of the check valve 32 is also connected to the second check valve 36, the output of which is connected to a sample pump 38, also driven by a stepping motor (not shown). The output of the check valve 36 and the sample pump 38 is connected to a thin flexible intake tube 40, the open end of which is connected to and guided by a lever arm 42 which is driven by an input tube servomotor 44 to be rotated as indicated by the dashed line 46 to thereby transfer the open end of the intake tube 40 from a vessel, such as the rinsing vessel 28 to the sample input aperture 48 of a graphite tube atomizer 50 of an atomic absorption spectrometer 52.

A control system 54 is coupled to and controls the functions of the spectrometer 52, intake tube servomotor 44, turntable servomotor 14, turntable carrier servomotor 20, and the stepping motors driving the sample pump 38 and the rinse pump 34. The operation of the prior art system of FIG. 1 is as follows. Upon initiation, the control system actuates the rinse pump 34 to draw in and discharge a small quantity of the rinsing solution through the intake tube 40 into the rinsing vessel 28. Intake tube servomotor 44 then lifts the lever 42 and its connected intake tube 40 from the rinsing vessel 28. The carrier servomotor 20 is actuated to position one of the vessels 12 under the end of the intake tube 40, the intake tube is then lowered into the vessel and the sample pump 44 withdraws a very small quantity of the sample liquid into the end of the intake tube. Intake tube servomotor 44 is then actuated to deposit the sample in the end of the intake tube 40 into the graphite tube 50. Simultaneously, the rinse pump 34 draws in a small supply of rinsing solution so that after the intake tube 40 is lifted from the graphite tube 50, the carrier servomotor 20 is actuated so that the intake tube may be flushed into the rinsing vessel 28. The cleaned intake tube 40 is then lifted and the turntable carrier is moved to position the reagent vessel 26 under the end of the tube. A small quantity of reagent is drawn into the intake tube and the servomotor 44 then repositions the tube to discharge its contents into the graphite tube atomizer 50. The control system 54 then actuates the power to the spectrometer 52 so that the contents of the graphite tube 50 will dry, decompose, atomize, and be analyzed in the conventional manner. In the meantime, the arm 42 is returned to the rinsing vessel 28 to be ready to start the next feeding cycle.

In the above described system, the vessels 12 mounted in the turntable 10 may contain the liquid samples to be analyzed, or an occasional vessel may contain a precalibrated solution of known analysis which will be injected into the graphite tube atomizer 52 to calibrate the operation of the spectrometer 52. In this prior art system, the servomotor 14 is rotated to sequentially position the vessels under the end of the intake tube 40. The particular position of the turntable 10 and also the position of the turntable carrier 16 is monitored by optical analog to digital encoders as described in the copending application.

Figures 2, 3:
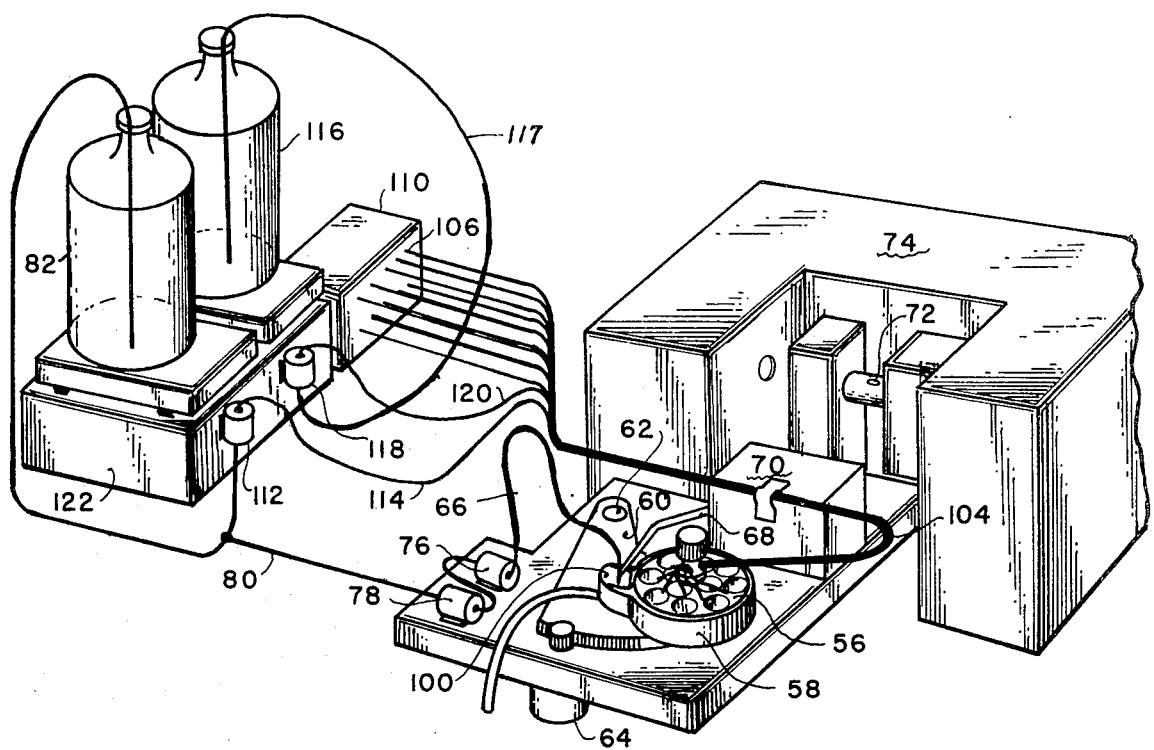
FIG. 2 is a perspective view of the present sample feeding apparatus.
FIG. 3 is a sectional cross-section view of a portion of the turntable of FIG. 2 illustrating the details of the drain channel, one overflow vessel, and input conduit thereto.

FIG. 2 is a perspective view illustrating the details of the improved sample feeding apparatus. The apparatus includes a turntable 56, similar to the turntable 10 of FIG. 1, containing a plurality of concentrically arranged sample vessels which will be subsequently described in greater detail. As with the embodiment of FIG. 1, the turntable 56, its housing 58 and the turntable servomotor 59 are mounted to a turntable carrier 60 that may be rotated about the pivot 62 by the carrier servomotor 64. Also in the manner similar to that described in connection with FIG. 1, the end of a sample input tube 66 is connected to a lever 68 which is controlled by the intake tube servomotor 70 and moves the end of the intake tube 66 between positions at the turntable and the sample opening of a graphite tube atomizer 72 in the atomic absorption spectrometer 74.

The opposite end of input tube 66 is connected to a sample pump 76 which operates in the same manner as the check valve 36 and sample pump 38 of FIG. 1 to apply suction or pressure to the intake tube 66. A rinse pump 78, which operates similarly to the valve 32 and pump 34 of FIG. 1, is connected via tubing 80 to a fluid container 82 containing a suitable rinsing solution so that upon actuation by an external control system (not shown) which is similar to the control system 54 of FIG. 1, the rinse pump 78 will flush the rinse fluid through the intake tube 66.

As illustrated in FIG. 2 and in greater detail in FIG. 3, the sample vessels, such as the vessel 84, in the turntable 56 are overflow vessels, each having a cylindrical wall 86 and a frustroconical interior bottom 88, the exterior bottom of which is preferably flat so that the entire vessel may be placed on a flat surface when removed from the turntable. Just above the junction of the internal frustroconical section and the internal cylindrical wall of the vessel 84 are one or more radial holes 90 to permit overflow draining of sample solutions from the vessel, and in the wall opposite the holes 90 is a port 92 into which is inserted an input conduit 94 for supplying solutions into the vessel 84.

Located beneath the turntable 56 and forming a part of the housing 58 is a drain channel 96 which receives the overflow from each of the overflow vessels in the turntable 56 and drains out through a tubing connector 98 into a suitable waste container. Forming a part of the housing 58 and the drain channel 96 is a rinse vessel 100 which, as best illustrated in FIG. 2, is moved with the turntable assembly on the carrier 60 to a point beneath the end of the intake tube 66 to provide a drain for the rinse solution forced through the intake tube.

Each overflow vessel, such as the overflow vessel 84 in the turntable 56, is supplied with a solution through their associated input conduit, such as the conduit 94. Each overflow vessel conduit extends through an appropriate bushing in the surface of the turntable 56 and through a radial hole through the base of a knob 102 and, as illustrated in FIG. 2, through a U-shaped loop 104 to corresponding ports 106 in a sample distribution unit 110 which may contain suitable pumping apparatus or which may be positioned above the surface of the turntable 56 for providing gravity flow through the various intake conduits.

Instead of providing a separate reagent vessel, such as the vessel 26 of FIG. 1, the dilutant or blank solution may be the same as the rinse solution used to flush the intake tube 66. Therefore, the rinse solution container 82 is coupled to a blank solution pump 112 which is operated by the control system (not shown) to inject at appropriate times a small amount of diluting solution through the input conduit 114 and into a selected one of the overflow vessels on the turntable 56. A second container 116 contains a precalibrated standard solution. This container is coupled by conduit 117 to the input of a standard solution pump 118, having an output connected to conduit 120, which leads to a selected one of the overflow conduits. The container 82 and 116 are mounted on platforms of a weight monitor 122, which is calibrated to produce an alarm signal, preferably an audio alarm, when the weight of either one of the containers 82 or 116 drops to a level that indicates that the solution therein is nearly exhausted.

The control system (not shown) is similar to the control system 54 of FIG. 1 and is programmed to control the operation of the spectrometer 72, sample pump 76, rinse pump 78, blank solution pump 112, standard solution pump 118, the turntable servomotor 59, the table carrier servomotor 64, and the intake tube servomotor 70. Because input conduits to the overflow vessels could become kinked, the turntable 56 is rotated no more than 360° and the turntable servomotor 59 is therefore bidirectionally controlled by the control system.

Operation of the system is similar but simpler than that of the prior art. Initially, the carrier servomotor 64 (FIG. 2) positions the end of the intake tube 66 over the rinse vessel 100 and rinse pump 78 flushes a small amount of solution from the rinse container 82 through the intake tube 66 and into the rinse vessel 100. Intake tube servomotor 70 then causes the lever 68 to lift the end of the rinsed tube 66 and the carrier servomotor 64 is energized to position the end of the intake tube over an appropriate overflow vessel in the turntable 56. It may be desired to start the operation by calibrating the spectrometer 74; in which case, the end of the intake tube 66 will be positioned over, and dipped into the overflow vessel that is supplied by the standard solution from container 116 and by pump 118 through conduit 120. Intake tube servomotor 70 then repositions the end of the intake tube 66 into the aperture in the graphite tube atomizer 72 and intake tube pump 76 is actuated to force the standard sample from the tube 66. Carrier servomotor 64 returns the turntable to the position shown in FIG. 2 and the intake tube servomotor 70 returns the intake tube to the rinse vessel 100, at which point the rinse pump 78 forces the rinse solution through the tube. The cycle is then repeated with an unknown sample solution in the selected overflow vessel. After the unknown sample has been injected into the graphite tube atomizer 72 and after the intake tube 66 has been flushed into the rinse vessel 100, the system selects the rinse vessel containing the blank solution and the appropriate quantity is drawn into the intake tube 66 and injected into the graphite tube 72 along with the unknown sample. The control system then energizes the spectrometer circuit and the sample is heated and atomized for analysis while, simultaneously, the feed apparatus is again flushing the intake tube and rotating the turntable in either direction to the next selected subsequent sample for analysis.

It is apparent, therefore, that the system is completely automatic so that a minimum of technician labor is required.

Having thus described the invention, what I claim is:

1. In combination with an atomic absorption spectrometer having a heatable sample atomizer with an aperture for receiving an injected liquid sample, an automatic sample feeding apparatus comprising:
    a rotatable turntable having therein a plurality of fluid containing vessels;
    an intake tube having a first end movable between a first position at said turntable and a second position at the aperture of the sample atomizer;
    pumping means connected with the second end of said intake tube, said pumping means for drawing in and injecting fluids from said first end of said intake tube; and
    control means coupled to said turntable, said first end of said intake tube, and to said pumping means for respectively positioning a selected one of said vessels on said turntable under said first intake tube end, dipping said first end into said selected vessel, drawing a fluid sample therefrom, transferring said first end to said second position at said sample aperture, and injecting said fluid sample therein;
    the improvement comprising:
        said fluid containing vessels are overflow vessels having at least one fluid overflow aperture in the wall thereof;
        an input conduit couples each of said overflow vessels with a source of fluid; and
        an annular drain channel is positioned under said turntable, said drain channel forming a housing for said turntable and providing a waste fluid outlet for fluids from said overflow vessels.

2. The sample feeding apparatus as set forth in claim 1 further including a blank solution supply container, a standard solution supply container, and pumping means operated by said control means for transmitting fluid samples from said supply containers through their respective input conduits to their respective overflow vessels in said turntable.

3. The sample feeding apparatus set forth in claim 2 wherein the contents of said blank solution container and said standard solution container are each monitored by sensing means that respond to the liquid level in each container and which produce output alarm signals when said contents drops below a predetermined level.

4. The sample feeding apparatus set forth in claim 3 wherein said liquid level sensing means are weight monitors that produce output alarm signals when the combined weight of a container and its contents drops below a predetermined level.

* * * * *